(12) United States Patent
Ke

(10) Patent No.: US 7,223,737 B1
(45) Date of Patent: May 29, 2007

(54) METHOD OF TREATING DRY EYE DISORDERS USING GLYCOSIDES

(75) Inventor: Tai-Lee Ke, deceased, late of Colleyville, TX (US); by Victor Ke, legal representative, Colleyville, TX (US)

(73) Assignee: Alcon, Inc., Hunenberg (CH)

( * ) Notice: Subject to any disclaimer, the term of this patent is extended or adjusted under 35 U.S.C. 154(b) by 10 days.

(21) Appl. No.: 11/200,739

(22) Filed: Aug. 10, 2005

Related U.S. Application Data

(60) Provisional application No. 60/601,211, filed on Aug. 13, 2004.

(51) Int. Cl.
*A61K 31/70* (2006.01)

(52) U.S. Cl. ......................... 514/24; 514/912

(58) Field of Classification Search ................... None
See application file for complete search history.

(56) References Cited

U.S. PATENT DOCUMENTS

| | | | |
|---|---|---|---|
| 4,131,651 A | 12/1978 | Shah et al. ................... 424/78 |
| 4,370,325 A | 1/1983 | Packman ................... 424/245 |
| 4,409,205 A | 10/1983 | Shively ........................ 424/78 |
| 4,744,980 A | 5/1988 | Holly .......................... 424/78 |
| 4,818,537 A | 4/1989 | Guo ........................... 424/427 |
| 4,883,658 A | 11/1989 | Holly .......................... 424/80 |
| 4,914,088 A | 4/1990 | Glonek et al. ................ 514/76 |
| 4,966,773 A | 10/1990 | Gressel et al. .............. 424/489 |
| 5,041,434 A | 8/1991 | Lubkin ....................... 514/182 |
| 5,075,104 A | 12/1991 | Gressel et al. ........... 424/78.04 |
| 5,174,988 A | 12/1992 | Mautone et al. .............. 424/45 |
| 5,278,151 A | 1/1994 | Korb et al. ................... 514/76 |
| 5,290,572 A | 3/1994 | MacKeen ................... 424/602 |
| 5,294,607 A | 3/1994 | Glonek et al. ................ 514/76 |
| 5,371,108 A | 12/1994 | Korb et al. ................. 514/762 |
| 5,405,878 A | 4/1995 | Ellis et al. .................... 422/28 |
| 5,538,721 A | 7/1996 | Babcock et al. .......... 424/78.04 |
| 5,578,586 A | 11/1996 | Glonek et al. ................ 514/76 |
| 5,597,808 A | 1/1997 | Haimes et al. ................ 514/33 |
| 5,631,004 A | 5/1997 | Cagle et al. ............. 424/78.04 |
| 5,696,166 A | 12/1997 | Yanni et al. ................. 514/573 |
| 5,780,467 A | 7/1998 | Dorn et al. ............... 514/236.2 |
| 5,800,807 A | 9/1998 | Hu et al. .................. 424/78.04 |
| 5,840,054 A | 11/1998 | Hamano et al. ................ 604/8 |
| 5,958,912 A | 9/1999 | Sullivan ..................... 514/177 |
| 5,985,259 A | 11/1999 | Cagle et al. ............. 424/78.04 |
| 6,022,862 A | 2/2000 | Haimes et al. ................ 514/33 |
| 6,153,607 A | 11/2000 | Pflugfelder et al. ......... 514/178 |
| 6,235,735 B1 | 5/2001 | Dorn et al. ............... 514/236.2 |
| 6,277,365 B1 | 8/2001 | Ellis et al. ............... 424/78.04 |
| 6,432,970 B2 | 8/2002 | Beachy et al. .............. 514/278 |
| 6,599,879 B1 | 7/2003 | Jimenez et al. ............... 514/12 |
| 6,630,135 B1 | 10/2003 | Cagle et al. ............. 424/78.04 |
| 6,638,930 B2 | 10/2003 | Dorn et al. ............... 514/236.2 |

FOREIGN PATENT DOCUMENTS

WO    WO 00/03705    1/2000

OTHER PUBLICATIONS

Lemp, "Report of the National Eye Institute/Industry Workshop on Clinical Trials in Dry Eyes," *CLAO Journal*, vol. 21(4), pp. 221-231 (1995).

McCulley et al., "Tear Film Structure and Dry Eye," *Contactologia* vol. 20, pp. 145-149 (1998).

Marsh et al., "Topical Nonpreserved Methylprednisolone Therapy for Keratoconjunctivitis Sicca in Sjogren Syndrome," *Ophthalmology*, vol. 106(4), pp. 811-816 (1999).

Shine et al., "Keratoconjunctivitis Sicca Associated with Meibomian Secretion Polar Lipid Abnormality," *Arch. Ophthalmol.* vol. 116, pp. 849-852 (1998).

Tauber et al., *Lacrimal Gland, Tear Film and Dry Eye Syndromes 2*, Plenum Press, New York (1998), "A Dose-Ranging Clinical Trial to Assess the Safety and Efficacy of Cyclosporine Ophthalmic Emulsion in Patients with Keratoconjunctivitis Sicca," pp. 969-972.

*Primary Examiner*—Zohreh Fay
(74) *Attorney, Agent, or Firm*—Patrick M. Ryan

(57) ABSTRACT

The topical use of glycosides for the treatment of dry eye disorders is disclosed.

6 Claims, No Drawings

METHOD OF TREATING DRY EYE DISORDERS USING GLYCOSIDES

This application claims priority to U.S. Provisional Application, U.S. Ser. No. 60/601,211 filed Aug. 13, 2004.

The present invention is directed to the treatment of dry eye disorders. In particular, the present invention is directed toward the use of glycosides to treat dry eye in mammals.

BACKGROUND OF THE INVENTION

Dry eye, also known generically as keratoconjunctivitis sicca, is a common ophthalmological disorder affecting millions of Americans each year. The condition is particularly widespread among post-menopausal women due to hormonal changes following the cessation of fertility. Dry eye may afflict an individual with varying severity. In mild cases, a patient may experience burning, a feeling of dryness, and persistent irritation such as is often caused by small bodies lodging between the eye lid and the eye surface. In severe cases, vision may be substantially impaired. Other diseases, such as Sjogren's disease and cicatricial pemphigoid manifest dry eye complications.

Although it appears that dry eye may result from a number of unrelated pathogenic causes, all presentations of the complication share a common effect, that is the breakdown of the pre-ocular tear film, which results in dehydration of the exposed outer surface and many of the symptoms outlined above (Lemp, *Report of the National Eye Institute/Industry Workshop on Clinical Trials in Dry Eyes, The CLAO Journal*, volume 21, number 4, pages 221-231 (1995)).

Practitioners have taken several approaches to the treatment of dry eye. One common approach has been to supplement and stabilize the ocular tear film using so-called artificial tears instilled throughout the day. Other approaches include the use of ocular inserts that provide a tear substitute or stimulation of endogenous tear production.

Examples of the tear substitution approach include the use of buffered, isotonic saline solutions, aqueous solutions containing water soluble polymers that render the solutions more viscous and thus less easily shed by the eye. Tear reconstitution is also attempted by providing one or more components of the tear film such as phospholipids and oils. Phospholipid compositions have been shown to be useful in treating dry eye; see, e.g., McCulley and Shine, *Tear film structure and dry eye, Contactologia*, volume 20 (4), pages 145-49 (1998); and Shine and McCulley, *Keratoconjunctivitis sicca associated with meibomian secretion polar lipid abnormality, Archives of Ophthalmology*, volume 116 (7), pages 849-52 (1998). Examples of phospholipid compositions for the treatment of dry eye are disclosed in U.S. Pat. No. 4,131,651 (Shah et al.), U.S. Pat. No. 4,370,325 (Packman), U.S. Pat. No. 4,409,205 (Shively), U.S. Pat. No. 4,744,980 and U.S. Pat. No. 4,883,658 (Holly), U.S. Pat. No. 4,914,088 (Glonek), U.S. Pat. No. 5,075,104 (Gressel et al.), U.S. Pat. No. 5,278,151 (Korb et al.), U.S. Pat. No. 5,294,607 (Glonek et al.), U.S. Pat. No. 5,371,108 (Korb et al.) and U.S. Pat. No. 5,578,586 (Glonek et al.). U.S. Pat. No. 5,174,988 (Mautone et al.) discloses phospholipid drug delivery systems involving phospholipids, propellants and an active substance.

Another approach involves the provision of lubricating substances in lieu of artificial tears. For example, U.S. Pat. No. 4,818,537 (Guo) discloses the use of a lubricating, liposome-based composition, and U.S. Pat. No. 5,800,807 (Hu et al.) discloses compositions containing glycerin and propylene glycol for treating dry eye.

Although these approaches have met with some success, problems in the treatment of dry eye nevertheless remain. The use of tear substitutes, while temporarily effective, generally requires repeated application over the course of a patient's waking hours. It is not uncommon for a patient to have to apply artificial tear solution ten to twenty times over the course of the day. Such an undertaking is not only cumbersome and time consuming, but is also potentially very expensive. Transient symptoms of dry eye associated with refractive surgery have been reported to last in some cases from six weeks to six months or more following surgery.

Aside from efforts directed primarily to the alleviation of symptoms associated with dry eye, methods and compositions directed to treatment of the dry eye condition have also been pursued. For example, U.S. Pat. No. 5,041,434 (Lubkin) discloses the use of sex steroids, such as conjugated estrogens, to treat dry eye conditions in post-menopausal women; U.S. Pat. No. 5,290,572 (MacKeen) discloses the use of finely divided calcium ion compositions to stimulate pre-ocular tear film production; and U.S. Pat. No. 4,966,773 (Gressel et al.) discloses the use of microfine particles of one or more retinoids for ocular tissue normalization.

Some recent literature reports suggest that patients suffering from dry eye syndrome disproportionately exhibit the hallmarks of excessive inflammation in relevant ocular tissues, such as the lacrimal and meibomian glands. The use of various compounds to treat dry eye patients, such as steroids [e.g. U.S. Pat. No. 5,958,912; Marsh, et al., *Topical nonpreserved methylprednisolone therapy for keratoconjunctivitis sicca in Sjogren syndrome, Ophthalmology*, 106 (4): 811-816 (1999); Pflugfelder, et. al. U.S. Pat. No. 6,153,607], cytokine release inhibitors (Yanni, J. M.; et. al. WO 0003705 A1), cyclosporine A [Tauber, *J. Adv. Exp. Med. Biol.* 1998, 438 (Lacrimal Gland, Tear Film, and Dry Eye Syndromes 2), 969], and 15-HETE (Yanni et. al., U.S. Pat. No. 5,696,166), has been disclosed.

SUMMARY OF THE INVENTION

The present invention is directed to methods for the treatment of dry eye. According to the methods of the present invention, a glycoside is topically administered to the eye of a patient. The topical composition administered according to the present invention comprises one or more glycosides as the only active ingredient(s). The topical compositions do not contain active ingredients for treating ocular disorders other than dry eye.

DETAILED DESCRIPTION OF THE INVENTION

Unless indicated otherwise, all component amounts are presented on a % (w/v) basis.

According to the methods of the present invention, a composition comprising a compound of formula (I) is topically administered to a mammal in need thereof:

$$R^1-Z-(R^2)_x \qquad (I)$$

wherein $R^1$ is $C_8$-$C_{28}$ aliphatic hydrocarbon, optionally unsaturated and optionally substituted with amino, hydroxyl, thiol, benzyl, phenyl, $CO_2R$, or a $C_3$-$C_6$ cycloalkyl where the cycloalkyl is optionally unsaturated;

R is a $C_1$-$C_4$ alkyl;

Z is O, C(O)O, OP(=O)$_2$O, S, or C(O)N;

$R^2$ is selected from the group consisting of glucoside, fructoside, galactoside, lactoside, sucroside and maltoside; and x is an integer from 1-10.

Preferred compounds of formula I are those wherein $R^1$ is a $C_8$-$C_{18}$ aliphatic hydrocarbon, optionally unsaturated and optionally substituted with amino, hydroxyl, thiol, benzyl, phenyl, $CO_2R$, or a $C_3$-$C_6$ cycloalkyl where the cycloalkyl is optionally unsaturated;

R is methyl or ethyl; and $R^2$ is selected from the group consisting of glucoside and maltoside.

The most preferred compound of formula I is dodecylmaltoside.

According to the methods of the present invention, a compound of formula I is administered in a pharmaceutically acceptable carrier for topical ophthalmic administration. The compositions are formulated in accordance with methods known in the art. The compositions may contain more than one compound of formula I.

The compositions of the present invention contain a pharmaceutically effective amount of a compound of formula I. As used herein, "a pharmaceutically effective amount" means an amount sufficient to reduce or eliminate dry eye symptoms. Generally, the compositions of the present invention will contain from 0.0001 to 0.01% of a compound of formula I. Preferably, the compositions of the present invention will contain 0.001%.

The compositions administered according to the present invention may also include various other ingredients, including but not limited to surfactants, tonicity agents, buffers, preservatives, co-solvents and viscosity building agents.

Various tonicity agents may be employed to adjust the tonicity of the composition, preferably to that of natural tears for ophthalmic compositions. For example, sodium chloride, potassium chloride, magnesium chloride, calcium chloride, dextrose and/or mannitol may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm).

An appropriate buffer system (e.g., sodium phosphate, sodium acetate, sodium citrate, sodium borate or boric acid) may be added to the compositions to prevent pH drift under storage conditions. The particular concentration will vary, depending on the agent employed. Preferably, however, the buffer will be chosen to maintain a target pH within the range of pH 5.5-8.

Other compounds designed to lubricate, "wet," approximate the consistency of endogenous tears, aid in natural tear build-up, or otherwise provide temporary relief of dry eye symptoms and conditions upon ocular administration to the eye are known in the art and may be included in the compositions of the present invention. Such compounds may enhance the viscosity of the composition, and include, but are not limited to: monomeric polyols, such as, glycerol, propylene glycol, ethylene glycol; polymeric polyols, such as, polyethylene glycol, hydroxypropylmethyl cellulose ("HPMC"), carboxy methylcellulose sodium, hydroxy propylcellulose ("HPC"), dextrans, such as, dextran 70; water soluble proteins, such as gelatin; and vinyl polymers, such as, polyvinyl alcohol, polyvinylpyrrolidone, povidone and carbomers, such as, carbomer 934P, carbomer 941, carbomer 940, carbomer 974P.

Topical ophthalmic products are typically packaged in multidose form. Preservatives are typically required to prevent microbial contamination during use. Suitable preservatives include: benzalkonium chloride, chlorobutanol, benzododecinium bromide, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% w/v. Unit dose compositions of the present invention will be sterile, but typically will not contain a preservative and will be unpreserved.

Generally, 1-2 drops of such compositions will be administered to each affected eye from once to many times per day.

Representative eye drop formulations are provided in Examples 1 and 2 below.

EXAMPLE 1

| Ingredient | Concentration (% w/v) |
| --- | --- |
| Dodecylmaltoside | 0.001 |
| Tromethamine | 0.05-0.15 |
| Boric Acid | 0.1-0.3 |
| Mannitol | qs 280-310 mOsm |
| Edetate Disodium | 0.01 |
| Benzalkonium Chloride | 0.01-0.015 |
| NaOH/HCl | q.s. to pH 6-8 |
| Purified Water | q.s. to 100 |

EXAMPLE 2

| Ingredient | Concentration (% w/v) |
| --- | --- |
| Dodecylmaltoside | 0.001 |
| Hydroxypropyl methylcellulose | 0.1-0.5 |
| Dextran 70 | 0.1 |
| Sodium Chloride | 0.8 |
| Potassium Chloride | 0.12 |
| Dibasic Sodium Phosphate | 0.025 |
| Edetate Disodium | 0.01 |
| Polyquaternium-1 | 0.001-0.005 |
| NaOH/HCl | q.s. to pH 6-8 |
| Purified Water | q.s. to 100 |

EXAMPLE 3

The ability of the compounds to treat dry eye is demonstrated in a mucin secretion assay using human primary corneal epithelial cells. A stock solution of 0.1% (w/v) n-Dodecyl-beta-D-maltoside (DDM) was prepared. The stock solution contained DDM in Keratinocyte Basal Medium ("KBM medium") supplemented with 0.5% (w/v) ethanol. The test compositions (0.01% DDM, 0.001% DDM, and 0.0001% DDM) were obtained by sequential 10-fold dilutions. The vehicle was used as a control (KBM medium supplemented with 0.05% ethanol).

Briefly, primary corneal epithelial cells derived from corneal cadaver tissue of a 52 year-old male were plated at a density of $2 \times 10^4$ cells/mL in a 24-well Biocoat plate (Becton Dickson, Rankin Lakes, N.J.) and grown in Keratinocyte Growth Media (Cambrex, Walkersville, Md.) ("KGM medium"). Culture medium was removed one day following cell passage and fresh KGM medium was added. A similar change of culture medium was done two days later. On day 6, culture medium was replaced with KBM medium that was supplemented with 1.5 mM $CaCl_2$. Upon 30 minutes of incubation at 37° C. medium was removed and fresh, ice-cold KBM medium containing 0.05% ethanol was added to the cells. Immediately thereafter cultures received appropriate amounts of vehicle, test- or reference compound.

Following a 45-minute incubation at 37° C., media was collected for determination of mucin released into the conditioned medium (soluble mucin). Adherent cells were then treated for a period of 10 minutes with 1% N-acetyl-L-cysteine (NAC 1%) dissolved in phosphate buffered saline (PBS). The NAC containing conditioned medium was removed for determination of membrane-associated mucin. Replicate samples of a mucin standard containing known quantities of Ca-15-3 (DF-3 antibody defined antigen), appropriate aliquots of conditioned culture media, and NAC cell washings were placed in the dot blot apparatus and allowed to collect on the nitrocellulose membrane by gravity flow. Upon sample application non-specific binding of peroxidase-linked *ricinus communis* agglutinin ($RCA_{120}$, Sigma Chemicals, St. Louis Mo.) to the nitrocellulose membrane was blocked by treatment with a 1% Tween-20 solution in Tris buffered (20 mM) saline (500 mM) (TTBS) (pH 7.5). Membranes were then stained with peroxidase-linked $RCA_{120}$ (1 μg/mL TTBS) and reacted with a buffered solution containing 3,3'-diaminobenzidine (DAB) co-substrate and hydrogen peroxide according the procedure supplied by the manufacturer of the peroxidase assay kit (Vector Laboratories, Burlingame, Calif.). Blots were air dried and scanned and optical densities determined.

The results are shown in Table 1. The Stimulation Index is the ratio of the Total Mucin Units/well for the test solution to the Total Mucin Units/well for the Control solution.

TABLE 1

| | Control | Dodecylmaltoside | | |
| | | 0.01% | 0.001% | 0.0001% |
|---|---|---|---|---|
| Soluble Mucin Units/well | 8.5 ± 0.1 | 13.2 ± 0.5 | 24.7 ± 2.7 | 10 ± 0.6 |
| Total Mucin Units/well | 15.2 ± 0.9 | 30.17 ± 0.6 | 32.3 ± 2.9 | 18.7 ± 0.2 |
| Stimulation Index | 1.00 | 1.98 | 2.12 | 1.23 |

This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

What is claimed is:

1. A method for the treatment of dry eye in a mammal suffering from dry eye, which comprises topically administering to the eye of the mammal a composition comprising a pharmaceutically acceptable carrier and a pharmaceutically effective amount of a compound of formula I:

wherein
- $R^1$ is $C_8$-$C_{28}$ aliphatic hydrocarbon, optionally unsaturated and optionally substituted with amino, hydroxyl, thiol, benzyl, phenyl, $CO_2R$, or a $C_3$-$C_6$ cycloalkyl where the cycloalkyl is optionally unsaturated;
- R is a $C_1$-$C_4$ alkyl;
- Z is O, C(O)O, OP(=O)$_2$O, S, or C(O)N;
- $R^2$ is selected from the group consisting of glucoside, fructoside, galactoside, lactoside, sucroside and maltoside; and
- x is an integer from 1-10;
- provided that the composition does not contain an active ingredient for treating an ocular disorder other than dry eye.

2. The method of claim 1 wherein
- $R^1$ is $C_8$-$C_{18}$ aliphatic hydrocarbon, optionally unsaturated and optionally substituted with amino, hydroxyl, thiol, benzyl, phenyl, $CO_2R$, or a $C_3$-$C_6$ cycloalkyl where the cycloalkyl is optionally unsaturated;
- R is methyl or ethyl; and
- $R^2$ is selected from the group consisting of glucoside and maltoside.

3. The method of claim 2 wherein the compound of formula (I) is dodecylmaltoside.

4. The method of claim 1 wherein the pharmaceutically acceptable amount is from 0.0001 to 0.01% (w/v).

5. The method of claim 4 wherein the pharmaceutically acceptable amount is 0.001% (w/v).

6. The method of claim 1 wherein the pharmaceutically acceptable carrier comprises one or more ingredients selected from the group consisting of surfactants; tonicity agents; buffers; preservatives; co-solvents; and viscosity building agents.

* * * * *